United States Patent
Poulsen et al.

(10) Patent No.: US 9,084,888 B2
(45) Date of Patent: Jul. 21, 2015

(54) SYSTEMS AND METHODS FOR SEGMENTATION OF RADIOPAQUE STRUCTURES IN IMAGES

(75) Inventors: Per Rugaard Poulsen, Aabyhoej (DK); Walther Fledelius, Horsens (DK); Paul Keall, Greenwich (AU); Elisabeth Weiss, Williamsburg, VA (US); Jun Lu, Henrico, VA (US); Emily Brackbill, Wyomissing, PA (US); Geoffrey Hugo, Richmond, VA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 628 days.

(21) Appl. No.: 13/294,038

(22) Filed: Nov. 10, 2011

(65) Prior Publication Data

US 2013/0121551 A1 May 16, 2013

(51) Int. Cl.
*G06K 9/00* (2006.01)
*A61N 5/10* (2006.01)
*G06T 17/00* (2006.01)

(52) U.S. Cl.
CPC .............. *A61N 5/1049* (2013.01); *G06T 17/00* (2013.01); *A61N 2005/1061* (2013.01); *G06T 2210/41* (2013.01)

(58) Field of Classification Search
CPC ........... G06T 2207/10072–2207/10112; G06T 2211/40–2211/436; G06T 11/008; A61B 6/02–6/037; A61B 6/52–6/5294; G06K 2209/40–2209/403; G06K 2209/05; G06K 9/34

USPC .................................. 382/100, 128–132, 154
See application file for complete search history.

(56) References Cited

U.S. PATENT DOCUMENTS

| | | | |
|---|---|---|---|
| 7,818,045 B2 * | 10/2010 | Rietzel | 600/425 |
| 8,355,552 B2 * | 1/2013 | Schwartz et al. | 382/131 |
| 8,582,855 B2 * | 11/2013 | Koehler | 382/131 |
| 2004/0092786 A1 * | 5/2004 | Zaider et al. | 600/1 |

FOREIGN PATENT DOCUMENTS

DE 102008050570 * 4/2010

OTHER PUBLICATIONS

Aubin et al., "Robustness and precision of an automatic marker detection algorithm for online prostate daily targeting using a standard V-EPID", dated Jun. 25, 2003 (8 pages).

Buck et al., "Potential and limitations of the automatic detection of fiducial markers using an amorphous silicon flat-panel imager", Physics in Medicine and Biology, published on Mar. 5, 2003 (12 pages).

(Continued)

*Primary Examiner* — Shefali Goradia
(74) *Attorney, Agent, or Firm* — Vista IP Law Group, LLP

(57) ABSTRACT

A method of determining a model of a marker includes obtaining projection images, each of the projection images having an image of a marker that indicates a shape of the marker, determining binary images of the marker for respective ones of the projection images, and constructing a three-dimensional model of the marker using the binary images, the three-dimensional model comprising a set of voxels in a three-dimensional space that collectively indicates a three-dimensional shape of the marker, wherein the act of constructing the three-dimensional model is performed using a processing unit.

33 Claims, 15 Drawing Sheets

(56) References Cited

OTHER PUBLICATIONS

Carl et al., "Feasibility study using a Ni—Ti stent and electronic portal imaging to localize the prostate during radiotherapy", Radiotherapy and Oncology 78 (2006) 199-206, (8 pages).

Lu et al., "Four-dimensional cone beam CT with adaptive gantry rotation and adaptive data sampling", Med. Phys. 34 (9), Sep. 2007 (10 pages).

Nederveen et al., "Feasibility of automatic marker detection with an a-Si flat-panel imager", IOP Publishing Ltd., Physics in Medicine and Biology, Phys. Med. Biol. 46, 2011 (13 pages)).

Park et al., "Automatic marker detection and 3D position reconstruction using cine EPID images for SBRT verification", published Sep. 10, 2009 (11 pages).

Poulsen et al., "A Method to Estimate Mean Position, Motion Magnitude, Motion Correlation, and Trajectory of Atumor From Cone-Beam CT Projections for Image-Guided Radiotherapy", Int. J. Radiation Oncology Biol. Phys., vol. 72, No. 5, pp. 1587-1596, 2008 (10 pages).

Poulsen et al., "Real-time prostate trajectory estimation with a single imager in arc radiotherapy: a simulation study", Phys. Med. Biol. 54, dated 2009 (17 pages).

Poulsen et al., "Implementation of a New Method for Dynamic Multileaf Collimator Tracking of Prostate Motion in Arc Radiotherapy Using a Single KV Imager", Int. J. Radiation Oncology Biol. Phys., vol. 76, No. 3, pp. 914- 923, 2010 (10 pages).

Mao et al., "Fast internal marker tracking algorithm for onboard MV and kV imaging.systems", Department of Radiation Oncology, Stanford University School of Medicine, published Apr. 23, 2008 (8 pages).

Slagmolen et al., "Fast, accurate, and robust automatic marker detection for motion correction based on oblique kV or MV projection image pairs", published Mar. 15, 2010 (11 pages).

Carl et al., "A New Fiducial Marker for Gated Radiotherapy in the Lung—A Feasibility Study of Bronchoscopy Based Insertion and Removal in Göttingen Mini-Pig", Scand. J. Lab. Anim. Sci. 2010 vol. 37 No. 2 (11 pages).

\* cited by examiner

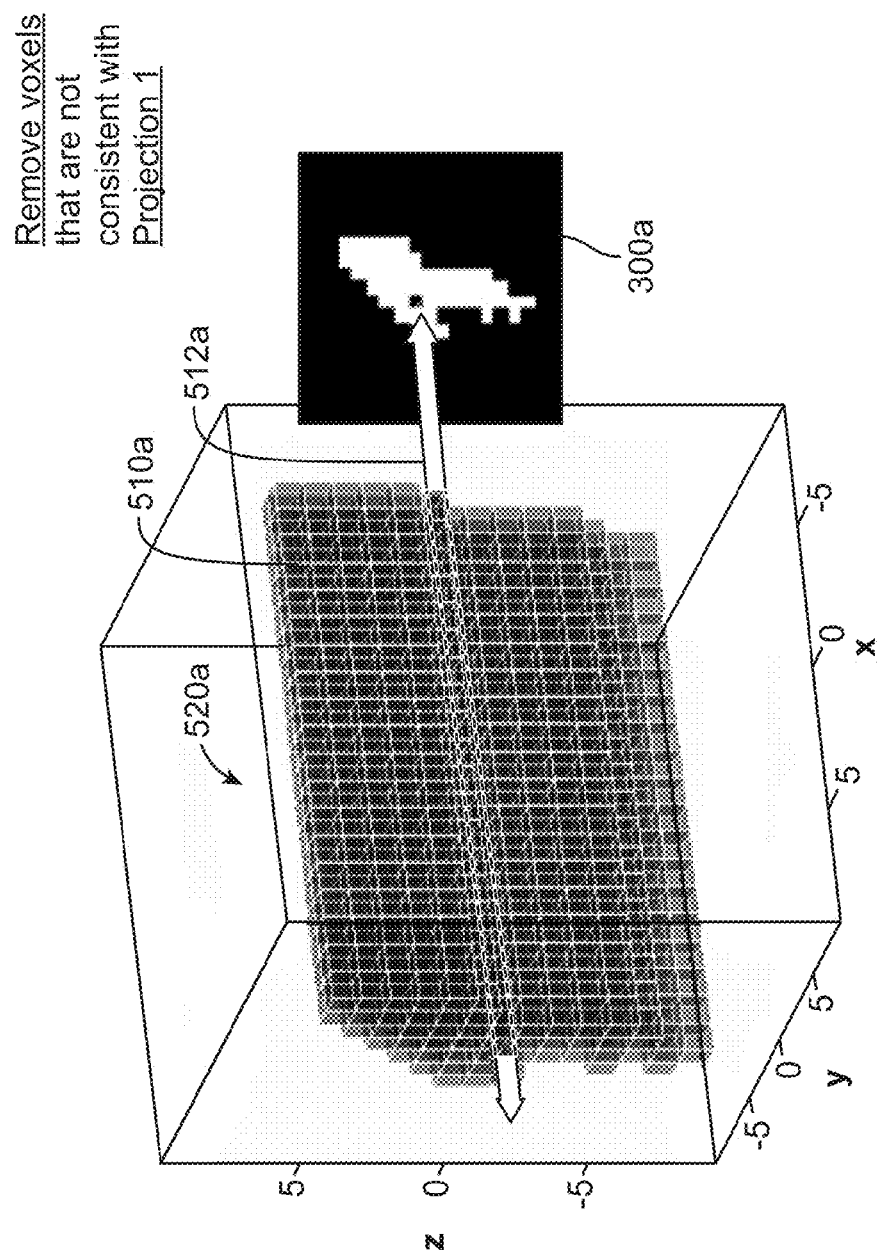

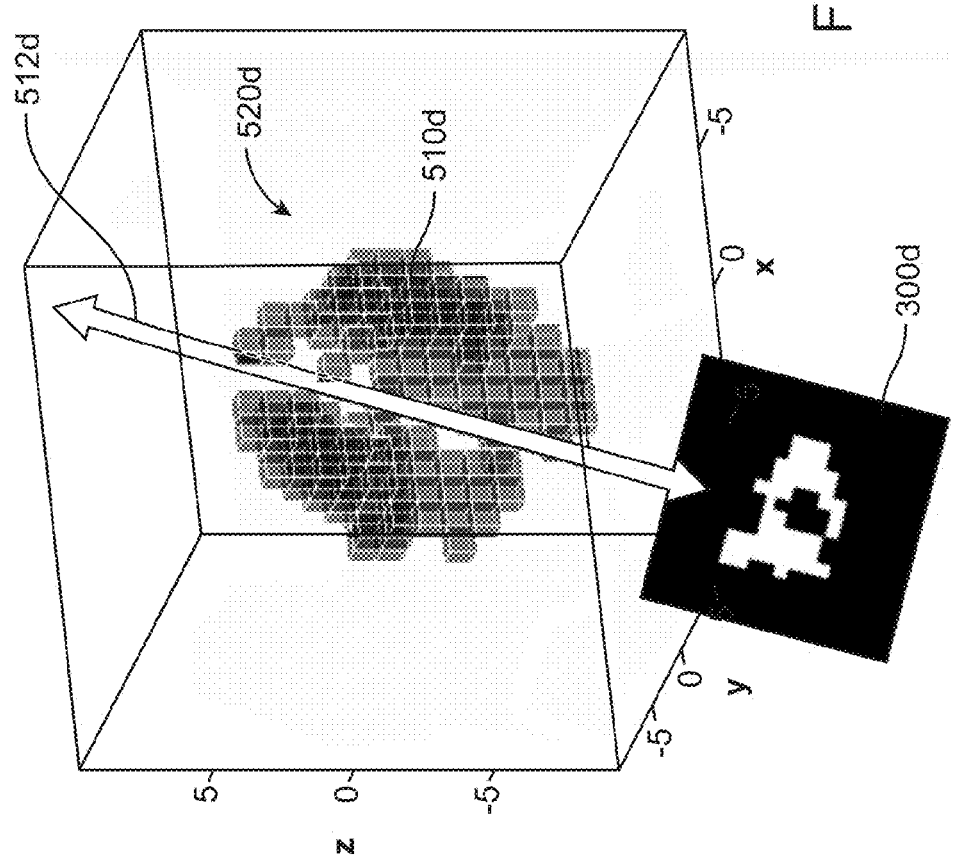

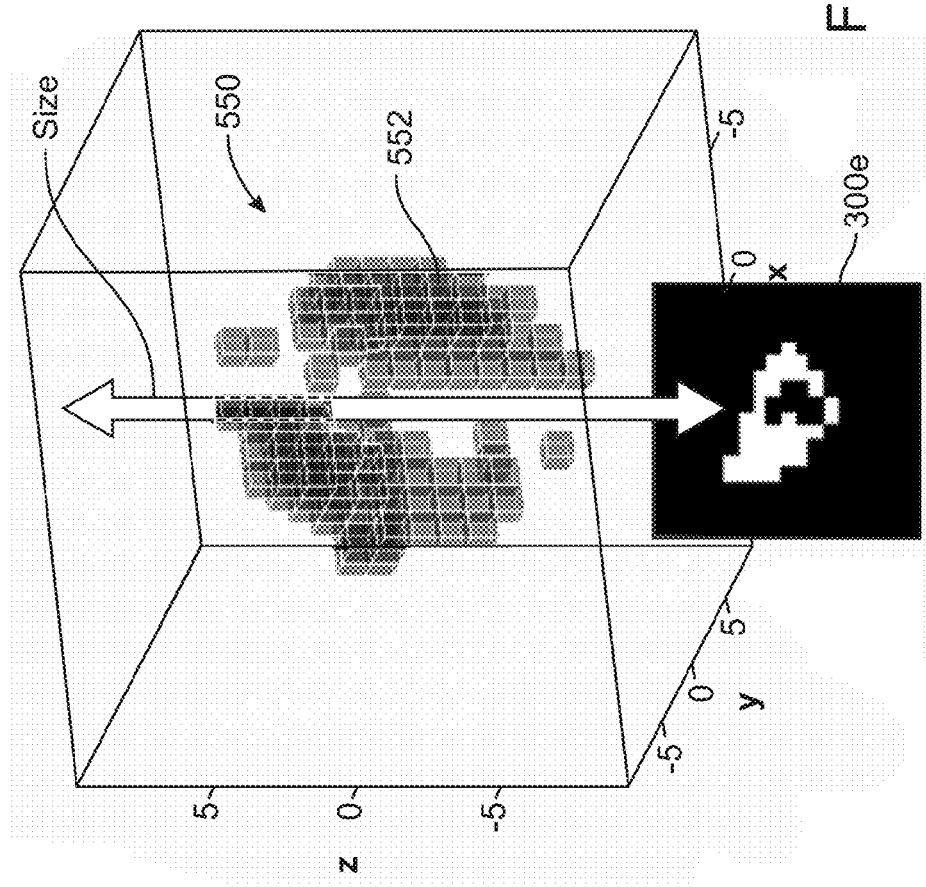

SYSTEMS AND METHODS FOR SEGMENTATION OF RADIOPAQUE STRUCTURES IN IMAGES

NOTICE OF GOVERNMENT SUPPORT

This invention was made with Government support under Grant No. P01 CA116602, awarded by the National Institutes of Health/National Cancer Institute. The Government has certain rights in this invention.

FIELD

This application relates generally to imaging, and more particularly, to systems and methods for segmentation of radiopaque structures in images.

BACKGROUND

Implanted markers have been used in radiotherapy for x-ray based target localization. The projected marker position in a series of cone-beam CT (CBCT) projections may be used to estimate a three dimensional target trajectory during the CBCT acquisition. Also, in radiotherapy, precise delivery of the treatment dose is crucial in order to maximize the ratio between tumour dose and normal tissue dose. To achieve this goal x-ray visible markers may be implanted in or near a tumour. It allows use of the projected marker trajectory in x-ray images for image-guided radiotherapy (IGRT).

However, Applicant of the subject application determines that reliable segmentation of the markers in the x-ray images may be difficult if the markers are irregularly shaped and/or viewed from varying directions such as in a cone-beam CT scan.

SUMMARY

In accordance with some embodiments, a method of determining a model of a marker includes obtaining projection images, each of the projection images having an image of a marker that indicates a shape of the marker, determining binary images of the marker for respective ones of the projection images, and constructing a three-dimensional model of the marker using the binary images, the three-dimensional model comprising a set of voxels in a three-dimensional space that collectively indicates a three-dimensional shape of the marker, wherein the act of constructing the three-dimensional model is performed using a processing unit.

In accordance with other embodiments, a system for determining a model of a marker includes a non-transitory medium storing projection images, each of the projection images having an image of a marker that indicates a shape of the marker, and a processing unit configured for determining binary images of the marker for respective ones of the projection images, and constructing a three-dimensional model of the marker using the binary images, the three-dimensional model comprising a set of voxels in a three-dimensional space that collectively indicates a three-dimensional shape of the marker.

In accordance with other embodiments, a computer program product includes a non-transitory medium storing a set of instructions, an execution of which will cause a process to be performed, the process comprising obtaining projection images, each of the projection images having an image of a marker that indicates a shape of the marker, determining binary images of the marker for respective ones of the projection images, and constructing a three-dimensional model of the marker using the binary images, the three-dimensional model comprising a set of voxels in a three-dimensional space that collectively indicates a three-dimensional shape of the marker.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIGS. 5A-5F illustrate a technique for constructing a three-dimensional model of a marker in accordance with some embodiments;

DESCRIPTION OF THE EMBODIMENTS

Figure 1:
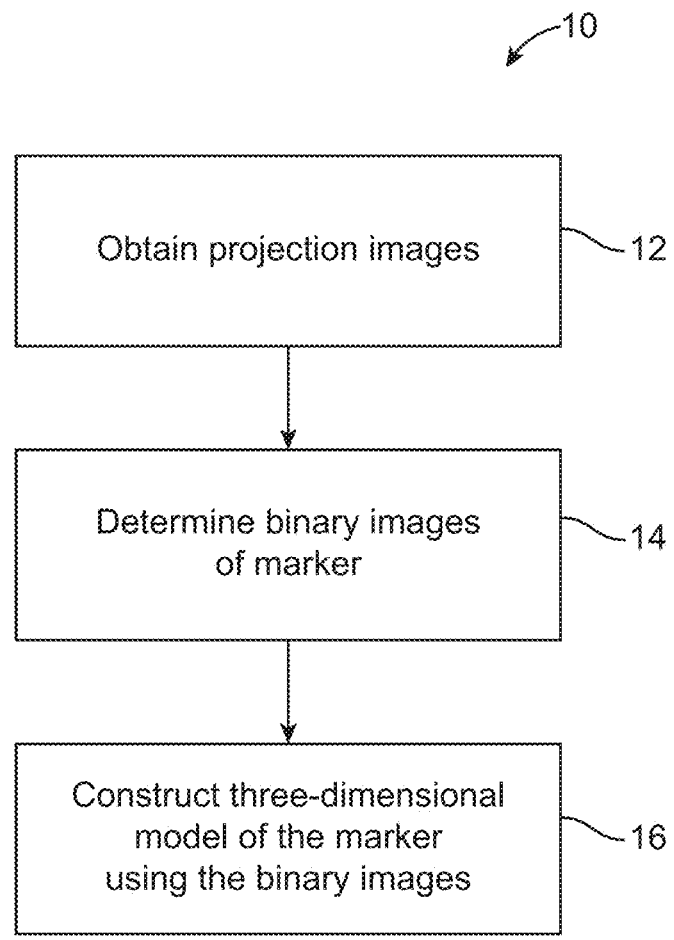
FIG. 1 illustrates a method of determining a model of a marker in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a method 10 of determining a model of a marker in accordance with some embodiments. In the illustrated embodiments, the marker may be an implanted marker that has been implanted in a patient. The marker may be a radiopaque marker, which is capable of being imaged by radiation (x-ray). In other embodiments, the marker may not be a radiopaque marker, and may have other features, as long as the marker is capable of being imaged using any type of imaging devices.

First, projection images are obtained (Item 12). In some embodiments, the projection images may be created using a radiation system that includes a moveable (e.g., rotatable) radiation source. By means of non-limiting examples, the radiation system may be a CT system (e.g., a CBCT system), a radiation treatment system, a PET system, a SPECT system, or any other system that is capable of generating images of an object from different positions. In the example of the CBCT system, the radiation source may rotate around the patient that has the implanted marker. While the radiation source is placed at different gantry positions around the object, the radiation source delivers radiation (e.g., in the form of half fan CBCT) towards the patient. The radiation exiting the patient is detected by a detector, which generates projection images in response to the detected radiation at different gantry positions. The projection images are then stored in a non-transitory medium for later processing.

In some embodiments, the act of obtaining the projection images may be performed by a processing unit, which receives the projection images from the detector (or from another device, such as a non-transitory medium storing the projection images). As used in this specification, the term "processing unit" may refer to one or more processing components, such as one or more processors. In the embodiments in which the processing unit includes multiple processors, the processors may be attached to a same platform (e.g., substrate), or may be communicatively coupled to each other (e.g., through cable(s) or wireless network(s)). Also, in some embodiments, the term "processor" may refer to a single processor, or to a processing system that includes one or more processors.

In other embodiments, the act of obtaining the projection images may include the act of creating the projection images. In such cases, the act of obtaining the projection images may be performed using the radiation system. Also, in some embodiments, the processing unit described herein may be considered to be a part of the radiation system.

In further embodiments, the act of obtaining the projection images may be performed automatically by the processing unit, which selects certain ones of the projection images from the set of all available projection images in accordance with some pre-defined criteria. For example, the processing unit may be configured to automatically select a prescribed number of projection images that have good contrast, have uniform background, and/or have large angular separation between the projection images. In one implementation, a projection image may be considered as having good contrast when the contrast of the marker image is above a prescribed contrast value. Also, in one implementation, the projection images may be considered as having large angular separation when gantry positions for the respective projection images are separated by at least 15 degrees, or other prescribed minimum value for the angular separation. In other embodiments, projection images without any disturbing background variations due to, e.g., bony anatomy or structures from a treatment couch or immobilization devices, may be selected. It should be noted that the criteria for selecting the projection images is not limited to the examples provided, and that other criteria may be used in other embodiments. Also, in further embodiments, more than one criterion (e.g., a combination of those described above) may be used to select the projection images.

In other embodiments, the selection of the projection images may be performed by a user, who manually selects the projection images from the set of all available projection images. In further embodiments, the selection of the projection images may be performed semi-automatically, in which the processing unit and the user both participate in the selection process.

Figure 2:
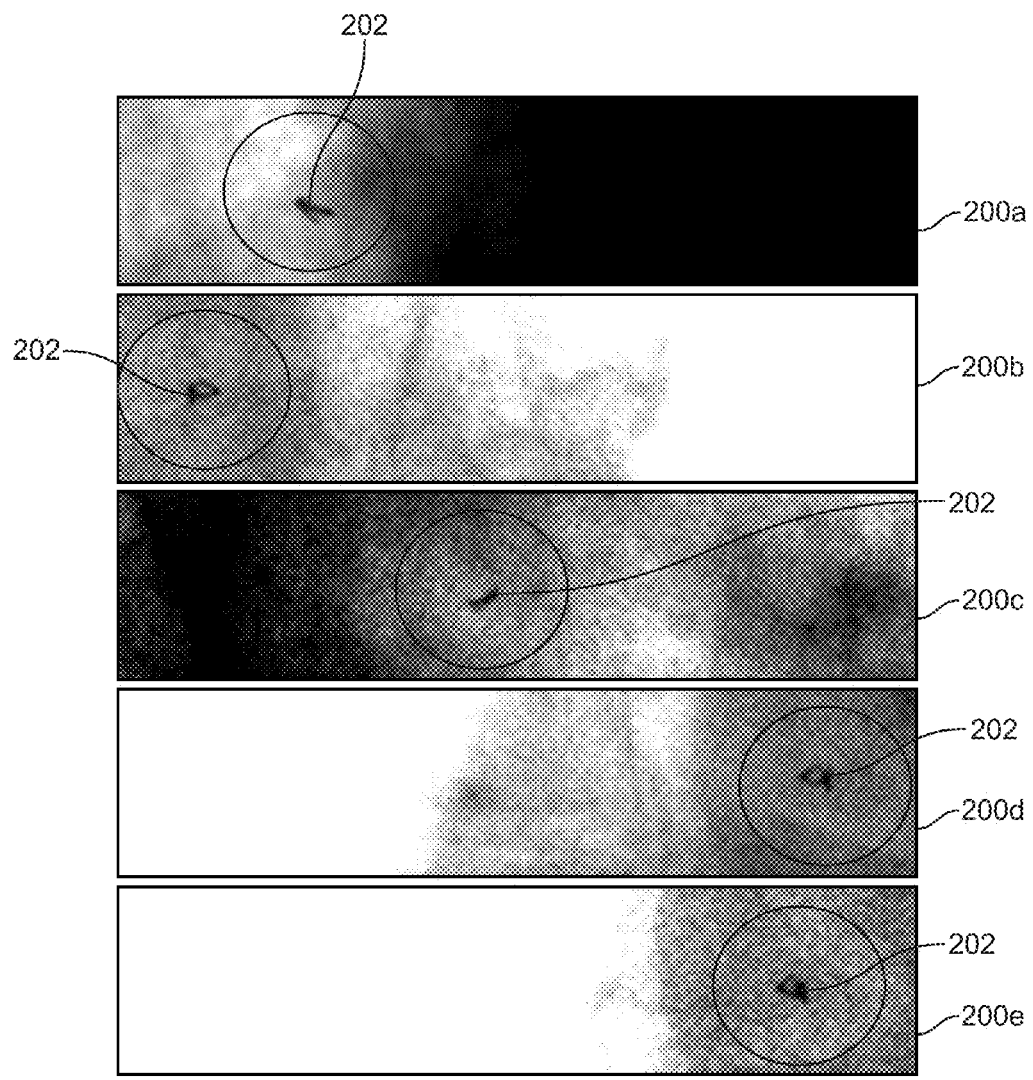
FIG. 2 illustrates examples of projection images of a marker in accordance with some embodiments.

FIG. 2 illustrates examples of selected projection images 200a-200e of a patient that has an implanted marker 202. The projection images 200a-200e are obtained at different respective gantry positions using a rotatable radiation source and a corresponding detector. Although five examples of the selected projection images 200a-200e are shown, in other embodiments, the processing unit and/or the user may select fewer or more than five projection images from the set of all available projection images. As shown in the figure, each of the projection images 200 includes an image of the marker 202, and indicates a shape of the marker 202. In the illustrated embodiments, the marker 202 has an irregular shape. Because the projection images 200a-200e are obtained from different gantry positions, the shape of the marker 202 appears different in the projection images 200a-200e. Because of the changing gantry position and respiratory induced marker motion between the acquisition of projection images 200a-200e, the marker 202 appears at different positions in the projection images 200a-200e.

Returning to the method 10 of FIG. 1, next, binary images of the marker for respective ones of the projection images are determined (Item 14). In some embodiments, threshold based segmentation technique may be employed by a processing unit to determine a set of voxels (e.g., pixels) in each two-dimensional projection image that are to be included for the binary image of the marker. For example, in some embodiments, a contrast threshold may be set. In such cases, any of the marker pixels in the projection image 200 with a contrast value that is greater than the contrast threshold will be included in the binary image for the marker 202. In other embodiments, the threshold may be set based on other characteristic(s) of the image. For examples, in other embodiments, the threshold may be an intensity threshold, a grey-scale threshold, or threshold for any of other types of image characteristics. In some embodiments, the setting of the threshold may be accomplished by a user entering an input to a processing unit (e.g., a processor, a software application, etc.). In other embodiments, the threshold may be set by programming the processing unit.

It should be noted that, as used in this specification, the term "binary image" is not limited to an image that represents a set of pixels that either contain or not contain the marker, and may refer to a set of pixels that represent probabilities of the pixels being parts of the marker. For example, in some embodiments, a first pixel in the binary image may have a value representing a 50% probability that the first pixel is a part of the marker, and a second pixel in the binary image may have a value representing a 75% probability that the second pixel is a part of the marker. In other examples, different pixels in the binary image may have other probability values.

Figure 3A:
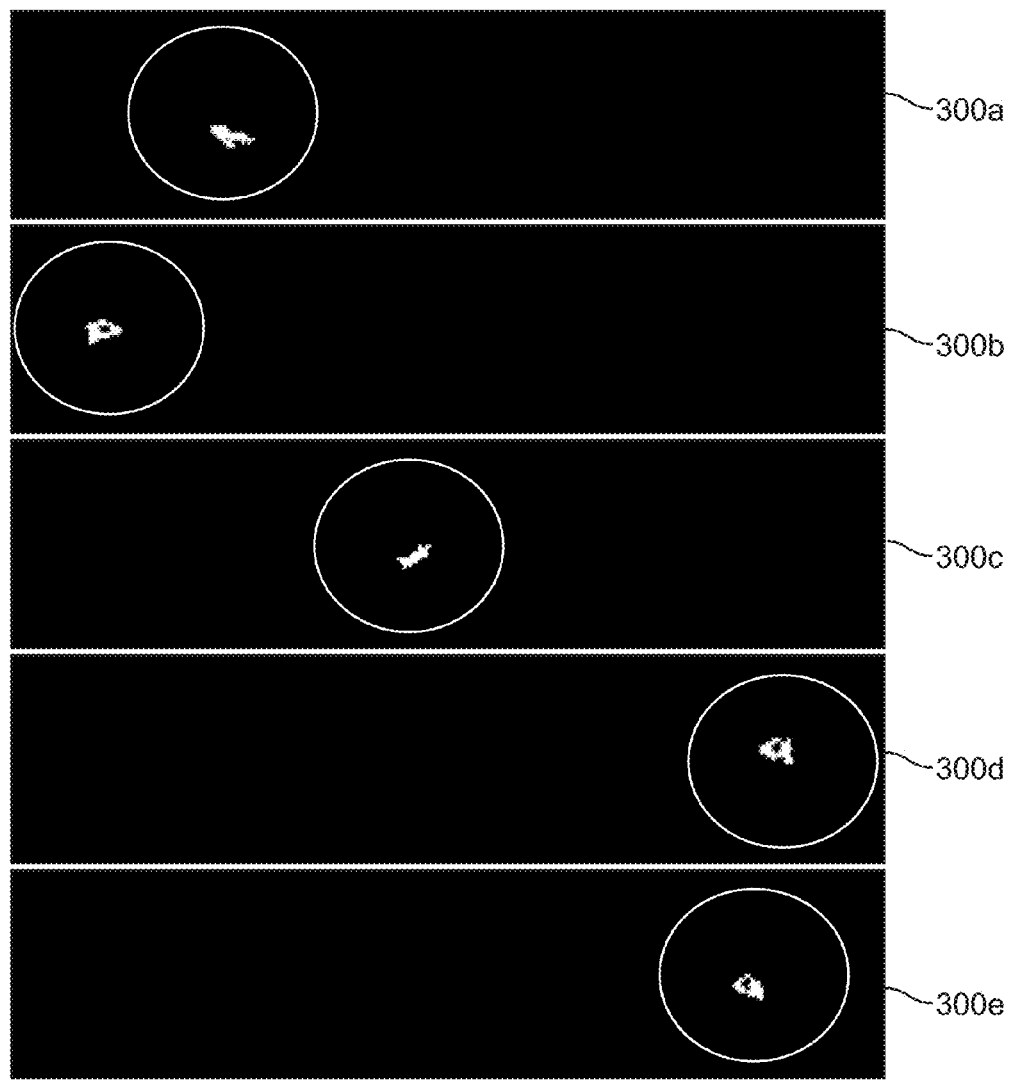
FIG. 3A illustrates binary images of the marker of FIG. 2 in accordance with some embodiments.
Figure 3B:
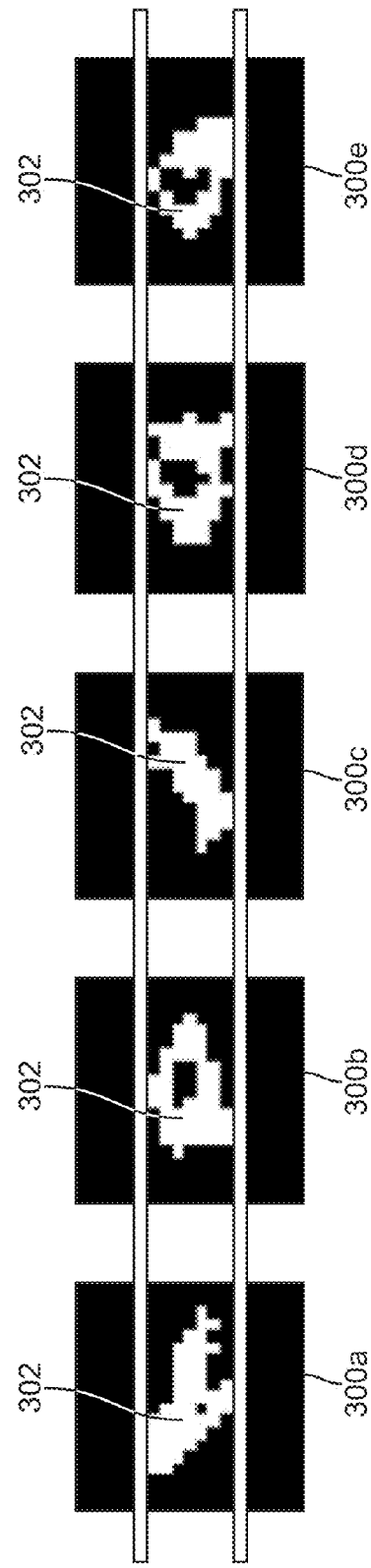
FIG. 3B illustrates the binary images of FIG. 3A in more detail after alignment.

FIG. 3A illustrates binary images 300a-300e of the marker 202 that have been formed from the projection images 202a-202e, respectively, of FIG. 2 based on threshold segmentation technique. FIG. 3B illustrates the binary images 300a-300e in further detail. As illustrated in the figure, in each of the projection images 200a-200b, certain ones of the pixels have been selected to be the marker pixels 302 for the binary image 300. In some embodiments, the binary images 300a-300e may be stored in a non-transitory medium for future use (e.g., processing).

Figure 4:
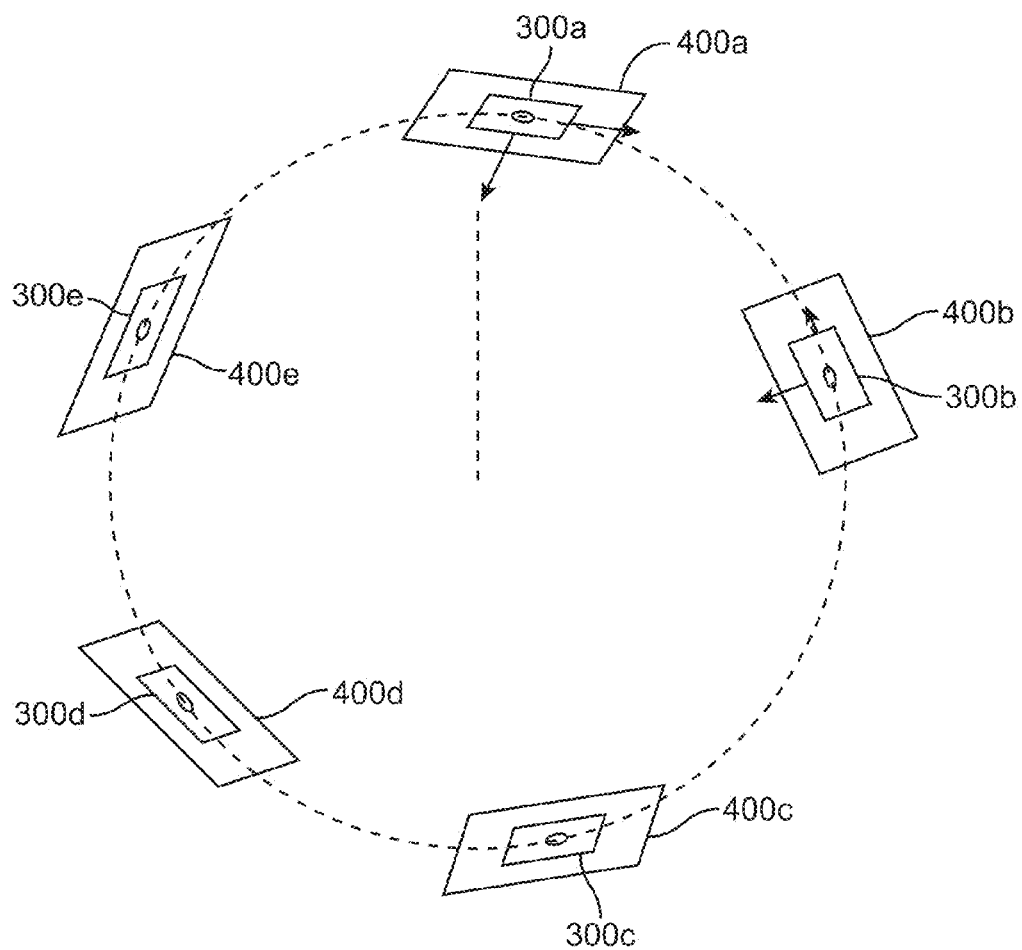
FIG. 4 illustrates alignment of the binary images of FIG. 3 in accordance with some embodiments.

As shown in FIG. 3B, the images 300a-300e have been aligned through an alignment process. In particular, after the binary images 300a-300e are obtained, one or more of the binary images 300a-300e may be moved to align them in order to account for real marker motion (e.g., due to breathing, etc.) and/or apparent marker motion caused by the imager rotating around a non-centered marker. FIG. 4 illustrates this concept. As shown in the figure, the binary images 300a-300e corresponds to different gantry angles at which the associated projection images 200a-200e are generated. The binary image 300a may be shifted within the plane 400a of the first projection image 200a in two directions (represented by the arrows). Similarly, the binary images 300b-300e may be shifted within the respective planes 400b-400c of the projection images 200b-200e, respectively. In one implementation, the alignment may be performed (e.g., by the processing unit) such that a central pixel, or a certain selected pixel at the same location of the marker, in all of the binary images 300a-300e coincide (e.g., lines extending from such pixel intersect). In other embodiments, instead of shifting the binary image 300, the binary image 300 may also be rotated within the respective plane 400 of the projection image 200. In other embodiments, if the projection images are generated while the imaged object is stationary, then the act of aligning the binary images 300 of the marker 202 may not be required. In further embodiments, if the marker 202 is non-rigid, and is subject to deformation (e.g., due to patient movement), portion(s) of the projection image 300 may be deformed to account for deformation of the marker 202. Also, in some embodiments, even for a stationary object, alignment may be performed if the marker is not positioned on the rotational axis of the imaging system. This is because an offset marker has an apparent motion—i.e., it will be shifted in one direction (e.g., in an anterior image), and in the opposite direction (e.g., in a posterior image).

Figure 5A:
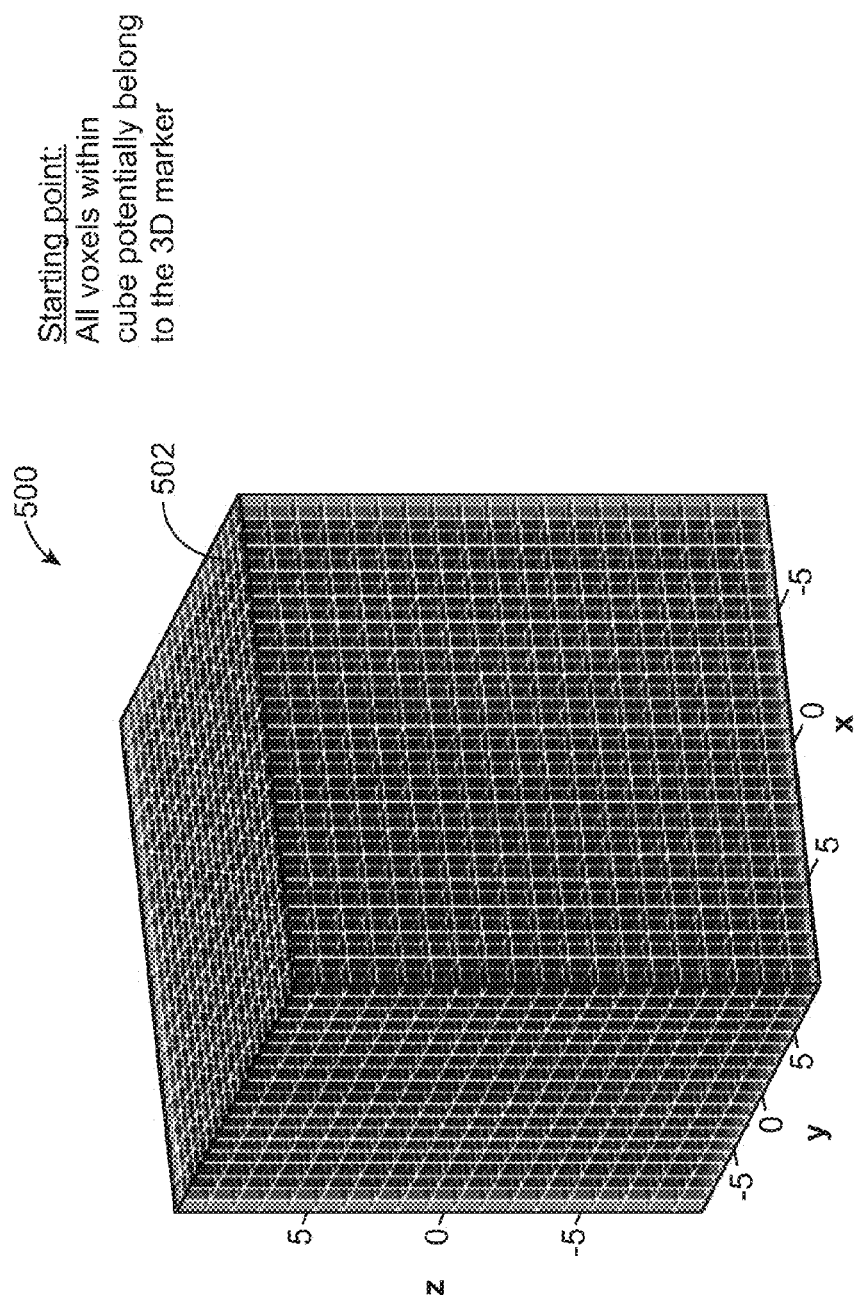

Returning to the method 10 of FIG. 1, next, a three-dimensional model of the marker is constructed using the binary images (Item 16). In the illustrated embodiments, the three-dimensional model includes a set of voxels in a three-dimensional space, wherein the set of voxels collectively indicates a three-dimensional shape of the marker. Various techniques may be used to construct the three-dimensional model from the binary images 300a-300e of the marker 202. FIGS. 5A-5E illustrate a technique for constructing a three-dimensional model of the marker 202 from the binary images 300a-300e using ray tracing technique. First, a three-dimensional space 500 in which the three-dimensional model is to be constructed may be defined (FIG. 5A). The three-dimensional space 500 includes voxels 502 that potentially belong to the three-dimensional model. In the illustrated embodiments, the voxels 502 are arranged in a three-dimensional configuration in the three-dimensional space 500. Also, in some embodiments, the coordinate space 500 may be modeled at a region that is surrounded by a rotational path of a radiation source. For example, in some embodiments, the coordinate space 500 may be defined to be located at an isocenter of a radiation system.

Next, the first binary image 300a of the marker 202 is used to determine a first set 510a of voxels in the three-dimensional space 500 that may potentially be included in the three-dimensional model of the marker 202 (FIG. 5B). In the illustrated embodiments, rays 512a (one is shown) from marker pixels in the binary image 300a are projected from the binary image 300a. The rays 512a are projected from a plane of the binary image 300a (which is the same plane as the plane of the corresponding projection image 200a from which the binary image 300a is derived), and extends in a direction that is perpendicular to the plane of the image 200a/300a. Because the plane of the binary image 300a/projection image 200a is at certain gantry angle, the set 510a of voxels formed by such ray tracing technique corresponds to the same gantry angle. As shown in the figure, all voxels in the coordinate space 500 that are intersected by the rays 512a from the binary image 300a form the first set 510a of voxels. The rest of the voxels in the space 500 is eliminated as potential candidates for the three-dimensional model of the marker 202. Thus, the first set 510a of voxels is a subset of all available voxels in the coordinate space 500, and form a first intermediate three-dimensional model 520a of the marker 202, which has a constant cross sectional shape corresponding to the shape of the marker 202 in the binary image 300a.

Figure 5C:
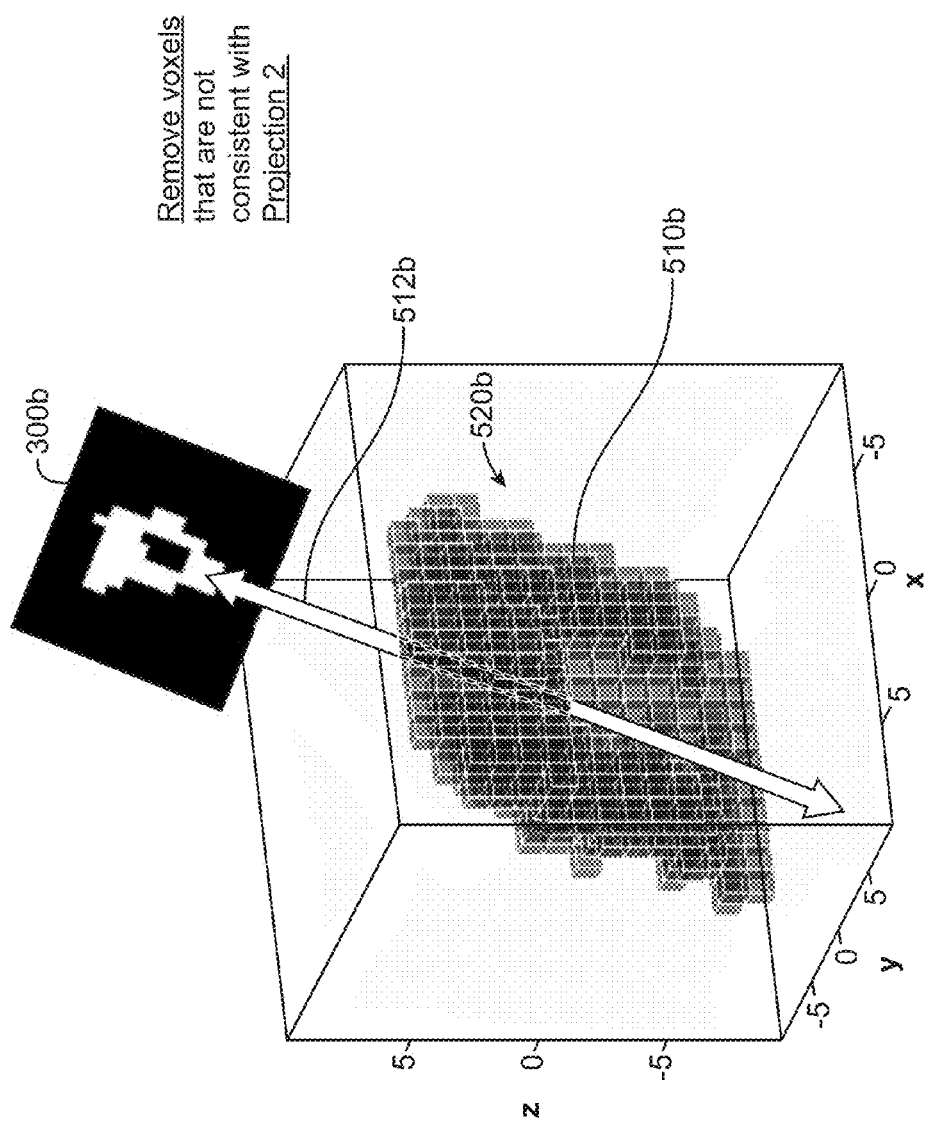

Next, the second binary image 300b of the marker 202 is used to determine a second intermediate three-dimensional model 520b of the marker 202, which includes voxels 510b that may potentially be included in the three-dimensional model of the marker 202 (FIG. 5C). In the illustrated embodiments, rays 512b (one is shown) from marker pixels in the second binary image 300b are projected from the second binary image 300b. The rays 512b are projected from a plane of the binary image 300b (which is the same plane as the plane of the corresponding projection image 200b from which the binary image 300b is derived), and extends in a direction that is perpendicular to the plane of the image 200b/300b. As shown in the figure, all voxels 510a in the first intermediate three-dimensional model 520a that are intersected by the rays 512b from the second binary image 300b form the second intermediate three-dimensional model 520b. The rest of the voxels in the first intermediate three-dimensional model 520a is eliminated as potential candidates for the three-dimensional model of the marker 202.

Figure 5D:
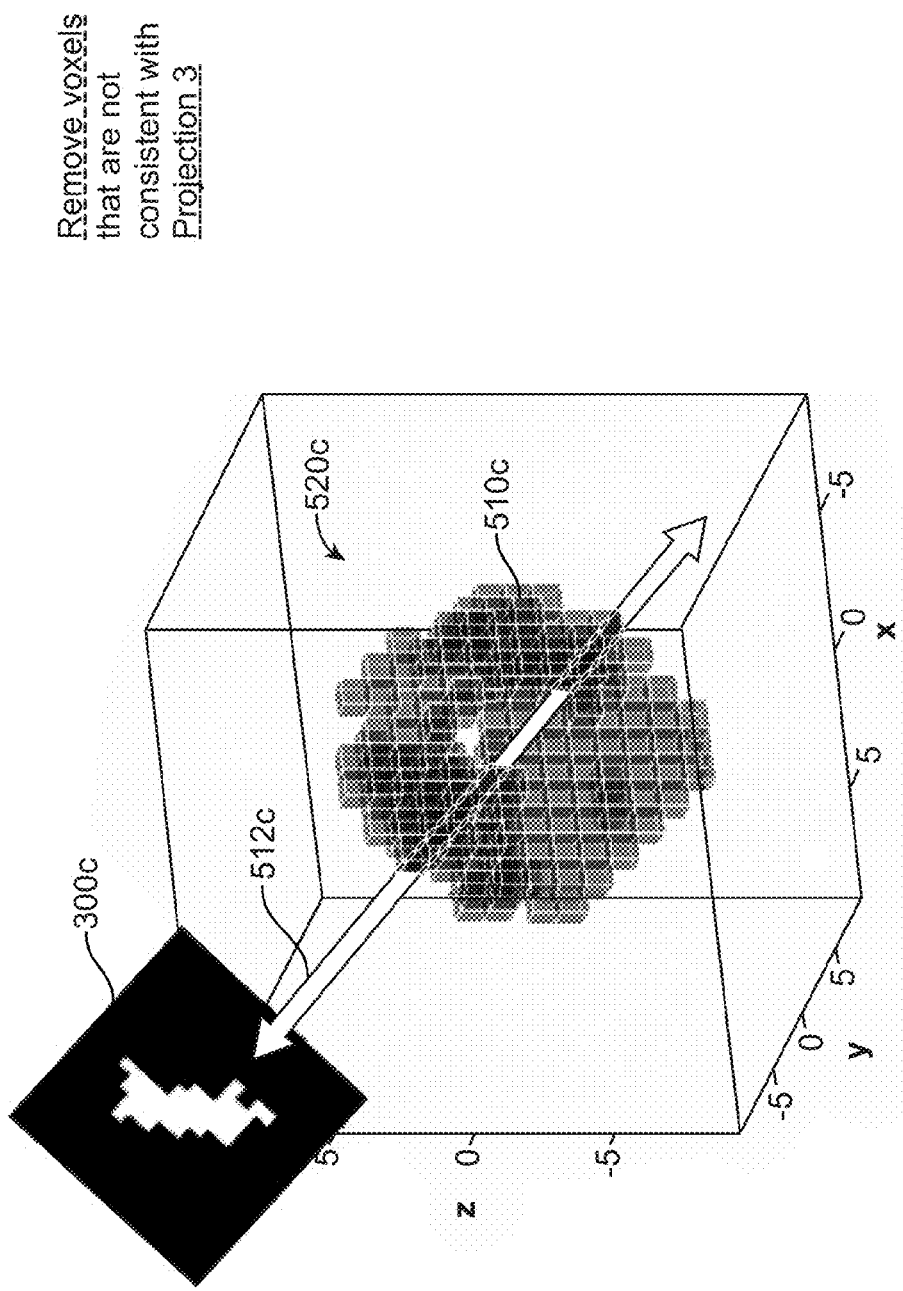

Next, the third binary image 300c of the marker 202 is used to determine a third intermediate three-dimensional model 520c of the marker 202, which includes voxels 510c that may potentially be included in the three-dimensional model of the marker 202 (FIG. 5D). In the illustrated embodiments, rays 512c (one is shown) from marker pixels in the third binary image 300c are projected from the third binary image 300c. The rays 512c are projected from a plane of the binary image 300c (which is the same plane as the plane of the corresponding projection image 200c from which the binary image 300c is derived), and extends in a direction that is perpendicular to the plane of the image 200c/300c. As shown in the figure, all voxels 510b in the second intermediate three-dimensional model 520b that are intersected by the rays 512c from the third binary image 300c form a third intermediate three-dimensional model 520c. The rest of the voxels in the second intermediate three-dimensional model 520b is eliminated as potential candidates for the three-dimensional model of the marker 202.

Next, the fourth binary image 300d of the marker 202 is used to determine a fourth intermediate three-dimensional model 520d of the marker 202, which includes voxels 510d that may potentially be included in the three-dimensional model of the marker 202 (FIG. 5E). In the illustrated embodiments, rays 512d (one is shown) from marker pixels in the fourth binary image 300d are projected from the fourth binary image 300d. The rays 512d are projected from a plane of the binary image 300d (which is the same plane as the plane of the corresponding projection image 200d from which the binary image 300d is derived), and extends in a direction that is perpendicular to the plane of the image 200d/300d. As shown in the figure, all voxels 510d in the third intermediate three-dimensional model 520c that are intersected by the rays 512d from the fourth binary image 300d form a fourth intermediate three-dimensional model 520d. The rest of the voxels in the third intermediate three-dimensional model 520c is eliminated as potential candidates for the three-dimensional model of the marker 202.

Next, the fifth binary image 300e of the marker 202 is used to determine the three-dimensional model 550 of the marker 202, which includes a set of voxels 552 for the marker 202 (FIG. 5F). In the illustrated embodiments, rays 512e (one is shown) from marker pixels in the fifth binary image 300e are projected from the fourth binary image 300e. The rays are projected from a plane of the binary image 300e (which is the same plane as the plane of the corresponding projection image 200e from which the binary image 300e is derived), and extends in a direction that is perpendicular to the plane of the image 200e/300e. As shown in the figure, all voxels 510d in the fourth intermediate three-dimensional model 520d that are intersected by the rays 512e from the fifth binary image 300e form the final three-dimensional model 550 of the marker 202. The rest of the voxels in the fourth intermediate three-dimensional model 520d is eliminated as candidates for the three-dimensional model 550 of the marker 202. In some embodiments, the three-dimensional model 550 may be stored in a non-transitory medium for future use (e.g., processing).

In the above embodiments, the three-dimensional model 550 has been described as being formed by progressively removing voxels in the space 500 that are not aligned with rays from the binary images 300. In other embodiments, the three-dimensional model 550 may be determined by simultaneously considering rays from two or more binary images 300. For example, in other embodiments, the three-dimensional model 550 may be constructed by determining (e.g., calculating) a matrix representing a set of voxels that are at the intersection of two or more sets of rays from two or more respective binary images 300. Accordingly, as used in this specification, "ray-tracing" technique/algorithm (or similar terms), or any reference made regarding determining intersection of rays, may refer to processing of rays sequentially or simultaneously, wherein such processing may be performed graphically, mathematically, or by other techniques. Also, the term "ray" (or similar terms) may refer to a hypothetical ray, wherein such hypothetical ray may be any parameter or feature that is derived from a binary image 300 based on projection/tracing of a pixel from the binary image 300.

As illustrated in the above example, the final three-dimensional model 550 of the marker 202 is formed by including voxels 552 that correspond with intersection of rays 512a-512e from the five binary images 300a-300e. In particular, rays 512 from each of the respective binary images 300a-300e form a respective set of projection voxels with a constant cross section that corresponds with the shape of the marker 202 in the respective one of the binary images 300a-300e. The final three-dimensional model 550 comprises voxels 552 that are those located at the intersection among the five sets of projection voxels.

In the above embodiments, the three-dimensional model 550 has been described as being formed using five binary images 300a-300e. In other embodiments, more than five binary images 300 may be used to construct the three-dimensional model 550. In further embodiments, the three-dimensional model 550 of the marker 202 may be constructed using less than five binary images 300 (e.g., three binary images 300).

In some embodiments, the three-dimensional model 550 may be constructed to have voxels with different properties for indicating a degree of certainty (accuracy) that the respective voxels belong to the model 550. For example, in some embodiments, all voxels in the model 550 that are obtained from intersection of rays from all five binary images 300a-300e may be assigned a value of "5", all voxels in the model 550 that are obtained from intersection of rays from only four of the five binary images 300a-300e may be assigned a value of "4", all voxels in the model 550 that are obtained from intersection of rays from only three of the five binary images 300a-300e may be assigned a value of "3", and all voxels associated with fewer than three intersecting rays may be excluded from the model 550. In such cases, the model 550 will include voxels having values ranging from 3-5. The higher value indicates that the corresponding voxel(s) is more likely to be accurate as part of the model 550. In other embodiments, the model 550 may include more than three values for the different voxels. Also, in other embodiments, the range of values may be different from the example described. In addition, in one or more embodiments, the different values for the different voxels in the model 550 may be represented by different colors.

In some embodiments, the determination of the three-dimensional model 550 may be performed by a processing unit, which uses the binary images 300 in an algorithm (e.g., a ray-tracing algorithm) to construct the three-dimensional model 550. For example, in some embodiments, the processing unit may be configured (e.g., built and/or programmed) to (1) determine a first set of voxels that corresponds with a first binary image of the marker 202, the first set of voxels aligned with rays projected from the first binary image, (2) determine a second set of voxels that corresponds with a second binary image of the marker 202, the second set of voxels aligned with rays projected from the second binary image, and (3) use intersection of the first and second sets of voxels to determine the set of voxels for the three-dimensional model 550. In some embodiments, these functions may be implemented by processing rays sequentially, as similarly discussed. In other embodiments, these functions may be implemented by processing rays simultaneously, as also similarly discussed. In further embodiments, the above functions may be implemented by calculating a first matrix representing the first set of voxels, calculating a second matrix representing the second set of voxels, and calculating a third matrix that represents intersection of voxels represented by the first and second matrices. In still further embodiments, the above functions may be implemented by calculating a matrix representing the three-dimensional model 550 using the binary images 300 of the marker 202. In such cases, the acts of determining the first and second sets of voxels are performed inherently in the calculation of the matrix.

In the above embodiments, the processing unit is configured to determine the three-dimensional model 550 without any prior-knowledge of the configuration (e.g., shape, size, material composition, etc.) of the marker 202. In other embodiments, information regarding the configuration of the marker 202 may be input to the processing unit to improve the efficiency of determining the three-dimensional model 550.

In some embodiments, the above technique for constructing the three-dimensional model 550 may be applied to achieve artifact-free image reconstruction of small metal objects (such as markers) in CBCT scans and CT scans. For example, in some cases, using the above technique, image/model of a metal object may be constructed without streaking artifacts (as may otherwise be seen in (CB)CT scans), without motion artifacts, and/or with a very high resolution (e.g., for example a voxel side length of 0.26 mm).

In some embodiments, after the three-dimensional model 550 is created, it may be used to determine a location of the marker 202. For example, in some embodiments, the three-dimensional model 550 may be used during an imaging process and/or a treatment process to determine a location of the marker 202. Also, in some embodiments, the determining of the location of the marker 202 may be repeated to thereby track the marker 202 locations over a period of time.

Figure 6:
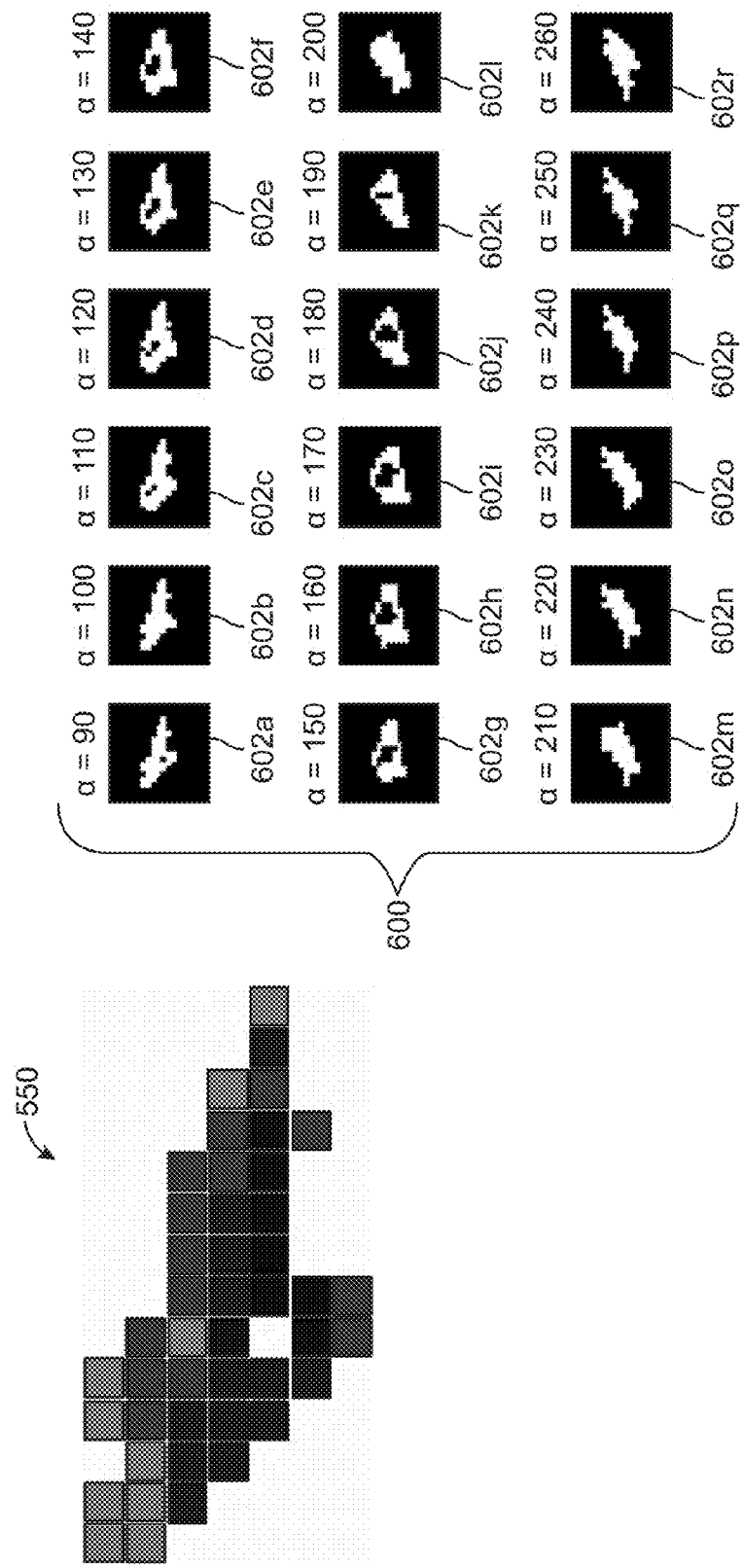
FIG. 6 illustrates templates derived from a three-dimensional model of a marker in accordance with some embodiments.

For determining marker location, a processing unit may first create a plurality of templates corresponding to different gantry angles by projecting the three-dimensional model 550 onto different respective planes at the corresponding gantry angles. FIG. 6 illustrates an example of a set 600 of templates 602 that are created by projecting the three-dimensional model 550 of the marker 202 onto different two-dimensional planes at different respective gantry angles α. In the illustrated example, the gantry angles α are separated by 10 degrees. In other embodiments, the gantry angles α may be separated by other angular/rotational spacing. In some embodiments, the templates 602 may optionally be smoothed by convolution with a Gaussian function. The templates 602 may be stored in a non-transitory medium for future use (e.g., processing).

In some cases, a marker may be offset (e.g., from an isocenter of a CBCT/imaging system). In such cases, a magnification factor may occur in a projection image that depends on the gantry/projection angle. In some embodiments, this may be accounted for by scaling the input projection images 200 before they are used by the processing unit to create the three-dimensional model 550, and by scaling the output templates 602 after the three-dimensional model 550 is created. In some embodiments, the scaling of the input projection images 200 and the scaling of the templates 602 may be performed by the processing unit based on a rough estimate of three-dimensional mean marker position. For example, in some embodiments, the rough estimate of the three dimensional mean marker position may be obtained from the projected marker position in the input projection images 200.

During a medical procedure (e.g., an imaging procedure and/or a treatment procedure), input images of a body part that contain the marker 202 may be obtained. In some embodiments, the input images may be obtained using x-rays. For examples, the input images may be projection images that may be obtained using the same machine that created the projection images for the three-dimensional model 550 of the marker 202. Alternatively, the input images may be projection images obtained using a different machine. In some cases, the input images may be obtained using a radiation source that is placed at different respective gantry positions. In such cases, for each input image that is obtained at a certain gantry angle, the processing unit looks up the stored templates 602, and retrieves one of the templates 602 that corresponds with the gantry angle at which the input image is obtained. For example, if the input image is obtained at an gantry angle of 36 degrees, the processing unit may retrieve one of the templates 602 that is obtained at a gantry angle closest to 36 degrees. Following the above example, the processing unit may retrieve a template 602 that is obtained at gantry angle equal to 36 degrees. In other embodiments, if the available templates 602 do not have one that corresponds to gantry angle equal to 36 degrees (for example, there may be one template corresponding to gantry angle being 30 degrees, and another one corresponding to gantry angle being 40 degrees), then the processing unit may pick the one that is the closest to that for the input image (in the example, the processing unit will pick the one template 602 corresponding to gantry angle being 40 degrees). In other embodiments, if the gantry angle at which the input image is generated is unknown, then the processing unit may perform image matching to select one of the available templates 602 best matches the input image.

In other embodiments, instead of creating a set of available templates 602 ahead of time, and selecting certain templates 602 from the available set, the processing unit may be configured to use the three-dimensional model 550 to generate templates 602 that correspond to the respective input images. For example, in one implementation, after an input image is obtained at a certain gantry angle α, the processing unit then projects the three-dimensional model 550 to an image plane that corresponds with the same gantry angle α to generate the template 602 for the respective input image. Such technique is advantageous because it ensures that the template 602 will always correspond with the input image.

Once the template 602 has been obtained (e.g., by generating it, or selecting it from a set of available templates) for the gantry angle of the input image, the processing unit may determine a marker location in the input image using the template 602. For example, in some embodiments, the processing unit may perform cross-correlation between the input image and the template 602 to identify a portion of the input image that best matches the selected template 602. In one implementation, the marker position may be determined as the position with the highest normalized cross correlation between the template 602, and the corresponding portion of the input image. This position may be found with a resolution of one pixel within a region of 40×40 pixels (or region of other sizes) centered at the projected marker position in the input image. In other embodiments, instead of performing cross-correlation, other techniques, such as image matching, etc., may be performed by the processing unit to identify the portion of the input image that best matches the selected template 602. The location of the identified portion in the input image may then be used as the location of the marker 202 in the input image. In some embodiments, if a machine coordinate system for the imaging machine that generated the input image is known, the processing unit may transform the determined location of the marker into a marker position in the machine coordinate system. Also, if the machine coordinate system relative to some arbitrary spatial coordinate system is known, the processing unit may also use such information to convert the marker location into a spatial coordinate in the arbitrary spatial coordinate system.

Figure 7:
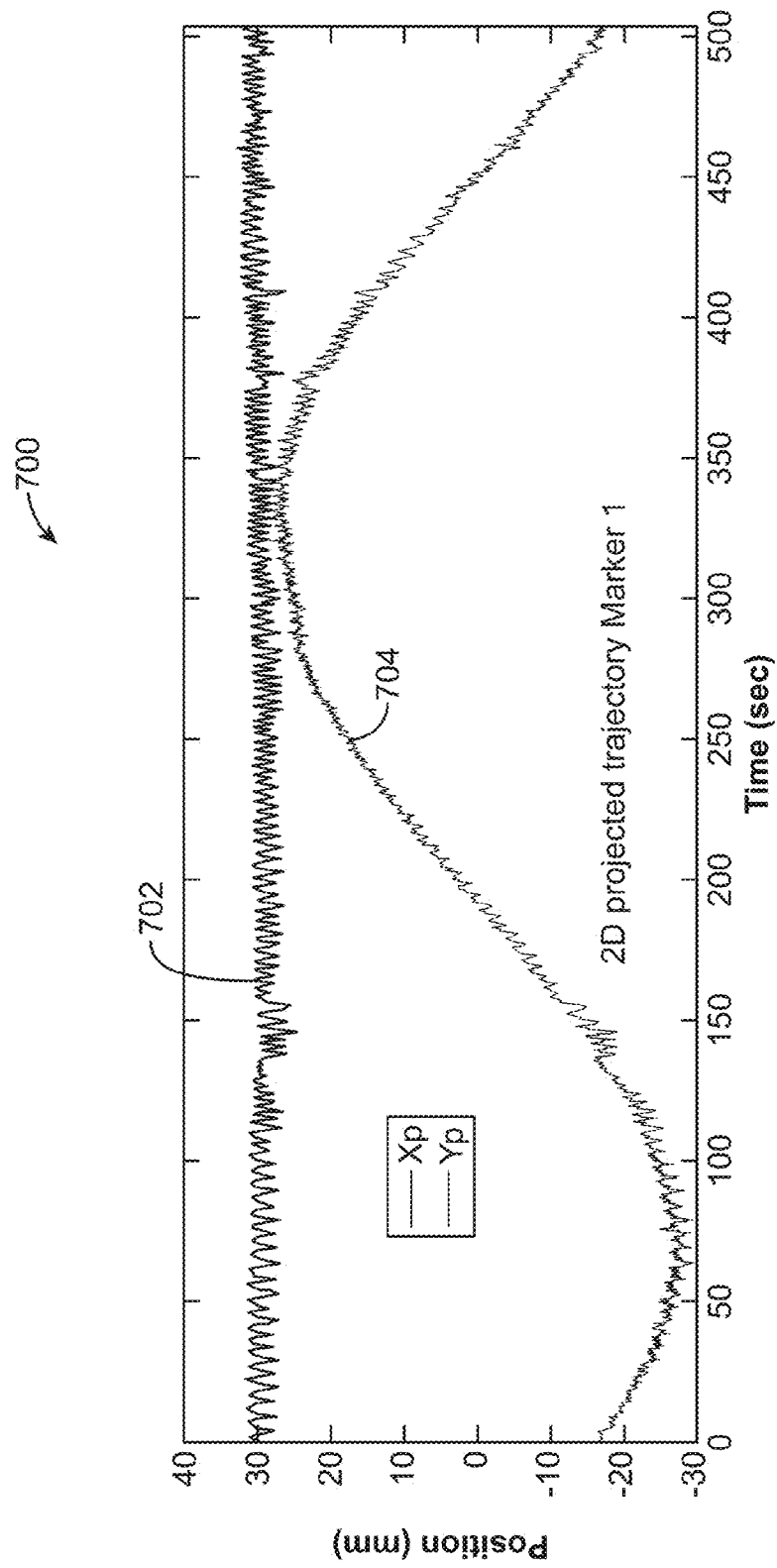
FIG. 7 illustrates a graph showing two-dimensional projected trajectory of a marker.

In some embodiments, the determined positions of the marker 202 through time may be plotted in a graph to see how the positions of the marker 202 vary in a sequence of input images. FIG. 7 illustrates a graph 700 showing the two-dimensional projected trajectory of the marker 202 in accordance with some embodiments. The x-coordinate represents time (or sequence of input images through time). The y-coordinate represents positions of marker 202 as determined by the processing unit using the above described technique. As shown in the figure, the graph 700 includes a first portion 702 showing the Y positions of the marker 202, and a second portion showing the X positions of the marker 202, which are determined by the processing unit (e.g., using the template technique described above).

In other embodiments, the processing unit may receive two input images that are generated simultaneously or close to each other in terms of time. The two input images may be generated at different respective gantry angles. In such cases, the processing unit may obtain two templates 602 (e.g., by generating them, or by selecting them from a set of available templates) that correspond best the two respective input images, and determine the marker positions in the two respective input images using the respective templates 602. The two marker positions may then be combined (e.g., using triangulation technique) to determine a three-dimensional coordinate for the marker 202.

It should be noted that the method for determining location of marker 202 using the template(s) 602 is not limited to the example described, and that other techniques may be used to determine the marker location in other embodiments.

In one or more embodiments described herein, the act of determining the marker location may be determined in real time (e.g., shortly after the input image is generated, such as within 5 seconds, and more preferably within 1 second, and even more preferably within a few milliseconds, after the input image is generated). In some embodiments, by repetitively determine the marker locations, a target object (e.g., tumor) may be tracked in real time. For example, in some cases, real-time segmentation may be done within 5-100 ms, which would allow for target tracking during radiotherapy treatment. In other embodiments, the act of determining the marker location may be performed long after the input image is generated (e.g., at least after 1 minute after the input image is generated).

In some embodiments, the determined marker location may be used to control an operation of a machine (e.g., an imaging and/or treatment machine, which may or may not involve use of radiation). For example, in a radiation treatment procedure, the determined marker location may correlate with a target location that is being treated by a radiation machine. When the marker location indicates that the target location is beyond a treatment position threshold, the radiation beam may be turned off (e.g., by a control unit, which may include the processing unit, or may be communicatively coupled to the processing unit). On the other hand, when the marker location indicates that the target location is within a treatment position threshold, the radiation beam may be turned on. Thus, the determined marker location may be used to turn a radiation beam on or off during a treatment procedure (e.g., as in a gating procedure to gate an operation of a treatment machine).

Also, in some embodiments, the determined marker location may be used to track a target (e.g., tumor). In one implementation, the determined marker location may be used for continuous realignment of a treatment machine with a target position. For example, a processor coupled to the treatment machine may be configured to adjust a position of a patient relative to the machine based on the determined marker location. In some embodiments, the processor may transmit a signal to move a patient support, to operate a collimator, to move a collimator, to tilt a gantry of the treatment machine, or combination of the foregoing.

The determined marker location may be used in other medical procedures in other embodiments.

In other embodiments, the determined three-dimensional model 550 may be used for other purposes. For example, in other embodiments, the three-dimensional model 550 may be used to obtain an image of the marker 202 without artifacts (e.g., motion artifacts (blurring), metal streaking artifacts, etc.). In some embodiments, the three-dimensional model 550 (or a part of it) may replace a part of an image that includes artifacts. For example, a x-ray image may include an artifact from a marker. In such cases, the three-dimensional model 550 of the marker may be projected to an image plane that corresponds with the x-ray image, and the projected image of the marker can be used to replace the portion of the x-ray image that includes the artifacts. In other embodiments, a constructed volumetric CT image may also include artifacts from a marker. In such cases, the three-dimensional model 550 of the marker may replace the portion of the volumetric CT image that includes the artifacts, thereby eliminating the artifacts. In one implementation, the replacement of the portion of an image that includes artifacts with the three-dimensional model 550 (or a projection of it) may be accomplished by superimposing or overlaying the image with the three-dimensional model 550 (or a projection of it).

It should be noted that embodiments of the method 10 described herein may be used to determine a three-dimensional model 550 for marker 202 having any arbitrary shape. For example, in some embodiments, the marker 202 may have an irregular shape (e.g., an asymmetric shape). Such marker 202 may have a rigid irregular shape that does not change after it is implanted. In other embodiments, the marker 202 may be flexible, and may change shape after it is implanted (e.g., due to physiological movement, such as heart movement, breathing movement, etc.).

Figure 8A:
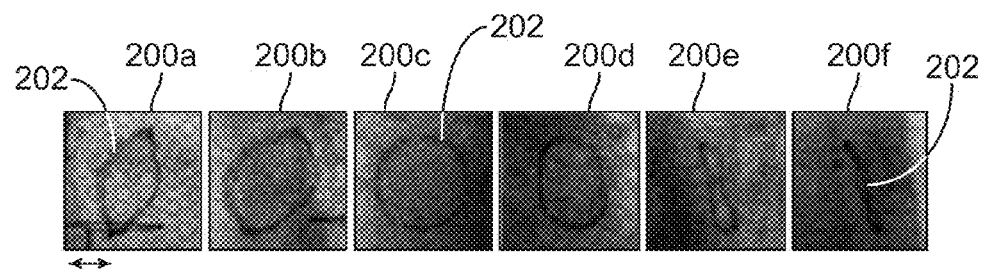
FIG. 8A illustrates projection images of another marker in accordance with other embodiments.
Figure 8B:
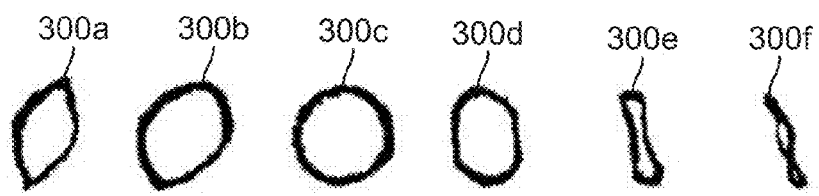
FIG. 8B illustrates binary images of the marker of FIG. 8A in accordance with some embodiments.
Figure 8C:
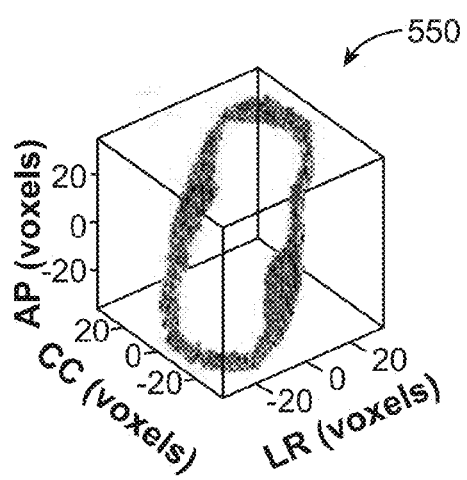
FIG. 8C illustrates a three-dimensional model of the marker of FIG. 8A in accordance with some embodiments.

Also, in other embodiments, the method 10 may be used to determine three-dimensional model 550 for any object having any arbitrary shape. Thus, as used in this specification, the term "marker" is not limited to an implanted device that is configured specifically for imaging purpose, and may refer to any object that is capable of being imaged. For example, in some embodiments, the object 202 may be an artificial cardiac valve. FIG. 8A illustrates different projection images 200a-200f of an artificial cardiac valve (which may be considered as an example of a marker). FIG. 8B illustrates corresponding binary images 300a-300f derived from the projection images 200a-200f, respectively. FIG. 8C illustrates the three-dimensional model 550 created using the binary images 300a-300f of FIG. 8B by applying a ray-tracing technique. In other embodiments, the marker/object 202 may be a coil, a stent, or other devices that are implanted in a patient. In further embodiments, the marker/object 202 may be a bodily structure (e.g., a dome of a diaphragm, the tumor itself, etc.). In still further embodiments, the marker/object 202 may be any substance that is injected into a patient, including oily contrast agent, such as lipiodol/ethiodol.

In the above embodiments, the marker segmentation method has been described with reference to constructing one three-dimensional model 550 for the marker 202. In other embodiments, the processing unit may be configured to construct two (or more) three-dimensional models 550 for the marker 202. For example, in other embodiments, the processing unit may be configured to generate different three-dimensional models 550 for different phases of a physiological cycle (e.g., breathing cycle). In one implementation, there may be a first model 550 for an inhale phase, and a second model 550 for an exhale phase. The processing unit may then generate two sets of templates 602, one from the first model 550 that corresponds with the inhale phase, and another one from the second model 550 that corresponds with the exhale phase. When determining marker location, the processing unit may receive an input image and a phase that is associated with the input image. If the phase of the input image indicates that the input image is generated when the patient is in the inhale phase, the processing unit then retrieves the first set of templates 602 for use to determine the location of the marker 202. On the other hand, in the example, if the phase of the input image indicates that the input image is generated when the patient is in the exhale phase, the processing unit then retrieves the second set of templates 602 for use to determine the location of the marker 202.

Also, in other embodiments, the processing unit may be configured to determine multiple three-dimensional models 550 for multiple respective markers 202. For example, in some embodiments, there may be multiple markers 202 in the patient. In such cases, one or more of the projection images 200 may show a plurality of markers 202. The processing unit may be configured to construct a three-dimensional model 550 for each marker 202 by choosing appropriate non-overlapping projections as input for the three-dimensional model 550. This would allow construction of joint templates 602 that encompass the overlapping markers 202, and enable segmentation and separation of the markers 202 from each other in the projection images.

Although the above embodiments have been described with reference to medical imaging, in other embodiments, the above techniques may be used in non-medical applications. For example, in other embodiments, three-dimensional model of an object may be obtained using embodiments of the technique described herein for non-destructive testing (e.g., for pipeline fault detection), security applications (e.g., for identification of suspicious objects in luggage and containers), etc. For example, in some embodiments, the above three-dimensional model 550 construction technique may be used to determine a model of an item that may potentially be a firearm, a weapon, a bomb, or other suspicious objects.

Computer System Architecture

Figure 9:
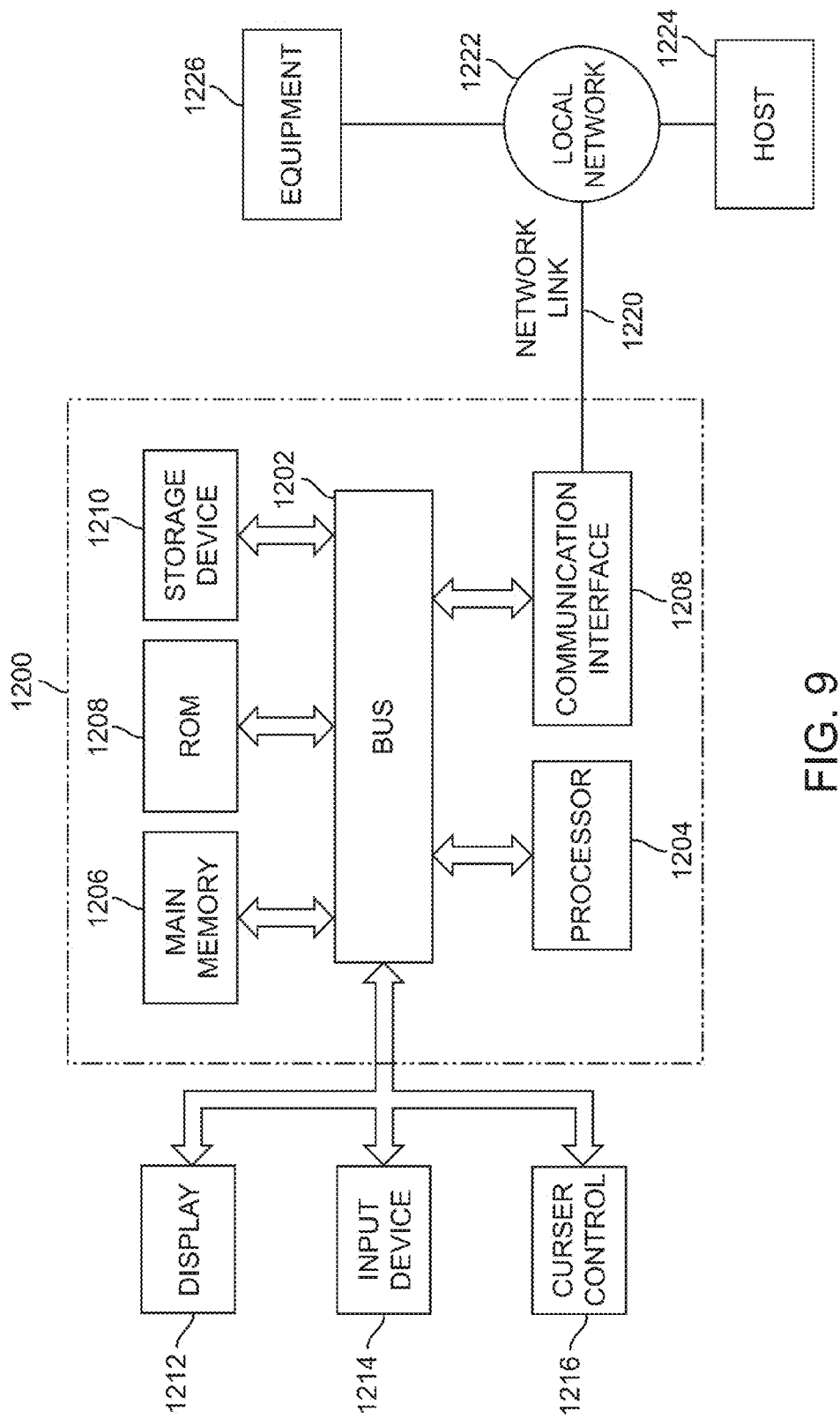
FIG. 9 illustrates a computer system with which embodiments described herein may be implemented in accordance with some embodiments.

FIG. 9 is a block diagram that illustrates an embodiment of a computer system 1200 upon which embodiments described herein may be implemented. For example, in some embodiments, the computer system 1200 may be used to implement the method 10 of constructing a three-dimensional model of a marker. In other embodiments, instead of or in addition to implementing the method 10, the computer system 1200 may be used to determine templates as described herein. In further embodiments, the computer system 1200 may be used to determine positions of the marker using the determined templates.

Computer system 1200 includes a bus 1202 or other communication mechanism for communicating information, and a processor 1204 coupled with the bus 1202 for processing information. The processor 1204 may be any of the embodiments of the processing unit described herein. The processor 1204 may be configured to perform various functions described herein. The computer system 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The computer system 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The computer system 1200 may be coupled via the bus 1202 to a display 1212, such as a cathode ray tube (CRT) or a flat panel, for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The computer system 1200 may be used for performing various functions (e.g., calculation) in accordance with the embodiments described herein. According to one embodiment, such use is provided by computer system 1200 in response to processor 1204 executing one or more sequences of one or more instructions contained in the main memory 1206. Such instructions may be read into the main memory 1206 from another computer-readable medium, such as storage device 1210. Execution of the sequences of instructions contained in the main memory 1206 causes the processor 1204 to perform the process steps described herein. One or more processors in a multi-processing arrangement may also be employed to execute the sequences of instructions contained in the main memory 1206. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1204 for execution. Such a medium may take many forms, including but not limited to, non-volatile media, volatile media, and transmission media. Non-volatile media (an example of non-transitory media) includes, for example, optical or magnetic disks, such as the storage device 1210. Volatile media (another example of non-transitory media) includes dynamic memory, such as the main memory 1206. Transmission media includes coaxial cables, copper wire and fiber optics, including the wires that comprise the bus 1202. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the computer system 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The computer system 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the computer system 1200, are exemplary forms of carrier waves transporting the information. The computer system 1200 can send messages and receive data, including program code, through the network (s), the network link 1220, and the communication interface 1218.

It should be noted that, as used in this specification, the term "image" is not necessarily limited to image that is displayed, and may refer to image that is not displayed as well. For example, in some embodiments, any of the images described herein (e.g., projection image 200, binary image 300, etc.) may be stored in a non-transitory medium as image data.

Although particular embodiments have been shown and described, it will be understood that they are not intended to limit the claimed inventions, and it will be obvious to those skilled in the art that various changes and modifications may be made without departing from the spirit and scope of the claimed inventions. The specification and drawings are, accordingly, to be regarded in an illustrative rather than restrictive sense. The claimed inventions are intended to cover alternatives, modifications, and equivalents.

What is claimed:

1. A method of determining a model of a marker, comprising:
    obtaining projection images, each of the projection images having an image of a marker that indicates a shape of the marker, the marker being a physical object implanted inside a patient;
    determining binary images of the marker for respective ones of the projection images; and
    constructing, using a processing unit, a three-dimensional model of the marker using the binary images, the three-dimensional model comprising a set of voxels in a three-dimensional space that collectively indicates an actual three-dimensional shape of the marker.

2. The method of claim 1, wherein the set of voxels for the three-dimensional model of the marker comprises a first voxel and a second voxel, wherein the first voxel has a first value associated therewith to indicate a first degree of certainty that the first voxel belongs to the three-dimensional model, and the second voxel has a second value associated therewith to indicate a second degree of certainty that the second voxel belongs to the three-dimensional model, the first value and the second value being different.

3. The method of claim 1, wherein the obtaining the projection images comprises:
    receiving a set of reference images; and
    selecting a subset of the reference images as the projection images;
    wherein two of the reference images in the selected subset have an angular separation that is at least 15 degrees; and
    wherein each of the two of the reference images in the selected subset has a marker contrast that is higher than a prescribed value.

4. A method for determining marker position, comprising creating a template using the three-dimensional model of the marker of claim 1.

5. The method of claim 4, wherein the template is created by projecting the three-dimensional model of the marker onto an image plane.

6. The method of claim 4, further comprising:
    receiving an input image;
    determining a maximum cross correlation between a part of the input image and the template; and
    using a position of the part of the input image to determine a position of the marker.

7. The method of claim 1, wherein the projection images comprise two-dimensional cone beam computed tomography (CT) projections.

8. The method of claim 1, wherein the three-dimensional model has an irregular configuration.

9. An image processing method that involves the three-dimensional model of claim 1, comprising:
    obtaining an image that includes an image artifact; and
    using the three-dimensional model to remove the image artifact.

10. The image processing of claim 9, wherein the using the three-dimensional model comprises replacing a part of the image that includes the image artifact with the three-dimensional model or with a projection of the three-dimensional model.

11. A method of determining a model of a marker, comprising:
    obtaining projection images, each of the projection images having an image of a marker that indicates a shape of the marker;
    determining binary images of the marker for respective ones of the projection images; and
    constructing, using a processing unit, a three-dimensional model of the marker using the binary images, the three-dimensional model comprising a set of voxels in a three-dimensional space that collectively indicates three-dimensional shape of the marker;
    wherein the act of constructing the three-dimensional model of the marker comprises:
        determining a first set of voxels that corresponds with a first one of the binary images of the marker, the first set of voxels aligned with rays projected from the first one of the binary images;
        determining a second set of voxels that corresponds with a second one of the binary images of the marker, the second set of voxels aligned with rays projected from the second one of the binary images; and
        using intersection of the first and second sets of voxels to determine the set of voxels for the three-dimensional model.

12. A system for determining a model of a marker, comprising:
    a non-transitory medium storing projection images, each of the projection images having an image of a marker that indicates a shape of the marker, the marker being a physical object implanted inside a patient; and
    a processing unit configured for
        determining binary images of the marker for respective ones of the projection images, and
        constructing a three-dimensional model of the marker using the binary images, the three-dimensional model comprising a set of voxels in a three-dimensional space that collectively indicates an actual three-dimensional shape of the marker.

13. The system of claim 12, wherein the set of voxels for the three-dimensional model of the marker comprises a first voxel and a second voxel, wherein the first voxel has a first value associated therewith to indicate a first degree of certainty that the first voxel belongs to the three-dimensional model, and the second voxel has a second value associated therewith to indicate a second degree of certainty that the second voxel belongs to the three-dimensional model, the first value and the second value being different.

14. The system of claim 12, wherein the processing unit is configured for obtaining the projection images by:
    receiving a set of reference images; and
    selecting a subset of the reference images as the projection images;
    wherein two of the reference images in the selected subset have an angular separation that is at least 15 degrees; and
    wherein each of the two of the reference images in the selected subset has a marker contrast that is higher than a prescribed value.

15. A system for determining marker position, comprising the processing unit of claim 12, wherein the processing unit is further configured for creating a template using the three-dimensional model of the marker.

16. The system of claim 15, wherein the processing unit is configured to create the template by projecting the three-dimensional model of the marker onto an image plane.

17. The system of claim 15, wherein the processing unit is further configured for:
    receiving an input image;
    determining a maximum cross correlation between a part of the input image and the template; and
    using a position of the part of the input image to determine a position of the marker.

18. The system of claim 12, wherein the projection images comprise two-dimensional cone beam computed tomography (CT) projections.

19. The system of claim 12, wherein the three-dimensional model has an irregular configuration.

20. A system for performing an image processing method that involves the three-dimensional model of claim 12, comprising the processing unit, wherein the processing unit is further configured for:
    obtaining an image that includes an image artifact; and
    using the three-dimensional model to remove the image artifact.

21. The system of claim 20, wherein the processing unit is configured for replacing a part of the image that includes the image artifact with the three-dimensional model or with a projection of the three-dimensional model.

22. A system for determining a model of a marker, comprising:
    a non-transitory medium storing projection images, each of the projection images having an image of a marker that indicates a shape of the marker; and
    a processing unit configured for
        determining binary images of the marker for respective ones of the projection images, and
        constructing a three-dimensional model of the marker using the binary images, the three-dimensional model comprising a set of voxels in a three-dimensional space that collectively indicates a three-dimensional shape of the marker;
    wherein the processing unit is configured for constructing the three-dimensional model of the marker by:
        determining a first set of voxels that corresponds with the a first one of the binary images of the marker, the first set of voxels aligned with rays projected from the first one of the binary images;
        determining a second set of voxels that corresponds with a second one of the binary images of the marker, the second set of voxels aligned with rays projected from the second one of the binary images; and
        using intersection of the first and second sets of voxels to determine the set of voxels for the three-dimensional model.

23. A computer program product having a non-transitory medium storing a set of instructions, an execution of which will cause a process to be performed, the process comprising:
    obtaining projection images, each of the projection images having an image of a marker that indicates a shape of the marker, the marker being a physical object implanted inside a patient;
    determining binary images of the marker for respective ones of the projection images; and
    constructing a three-dimensional model of the marker using the binary images, the three-dimensional model comprising a set of voxels in a three-dimensional space that collectively indicates an actual three-dimensional shape of the marker.

24. The computer program product of claim 23, wherein the set of voxels for the three-dimensional model of the marker comprises a first voxel and a second voxel, wherein the first voxel has a first value associated therewith to indicate a first degree of certainty that the first voxel belongs to the three-dimensional model, and the second voxel has a second value associated therewith to indicate a second degree of certainty that the second voxel belongs to the three-dimensional model, the first value and the second value being different.

25. The computer program product of claim 23, wherein the obtaining the projection images comprises:
    receiving a set of reference images; and
    selecting a subset of the reference images as the projection images;
    wherein two of the reference images in the selected subset have an angular separation that is at least 15 degrees; and
    wherein each of the two of the reference images in the selected subset has a marker contrast that is higher than a prescribed value.

26. The computer program product of claim 23, wherein the process further comprises creating a template using the three-dimensional model of the marker.

27. The computer program product of claim 26, wherein the template is created by projecting the three-dimensional model of the marker onto an image plane.

28. The computer program product of claim 26, wherein the process further comprises:
    receiving an input image;
    determining a maximum cross correlation between a part of the input image and the template; and
    using a position of the part of the input image to determine a position of the marker.

29. The computer program product of claim 23, wherein the projection images comprise two-dimensional cone beam computed tomography (CT) projections.

30. The computer program product of claim 23, wherein the three-dimensional model has an irregular configuration.

31. The computer program product of claim 23, wherein the process further comprises:
    obtaining an image that includes an image artifact; and
    using the three-dimensional model to remove the image artifact.

32. The computer program product of claim 31, wherein the using the three-dimensional model comprises replacing a part of the image that includes the image artifact with the three-dimensional model or with a projection of the three-dimensional model.

33. A computer program product having a non-transitory medium storing a set of instructions, an execution of which will cause a process to be performed, the process comprising:
 obtaining projection images, each of the projection images having an image of a marker that indicates a shape of the marker;
 determining binary images of the marker for respective ones of the projection images; and
 constructing a three-dimensional model of the marker using the binary images, the three-dimensional model comprising a set of voxels in a three-dimensional space that collectively indicates a three-dimensional shape of the marker;
 wherein the constructing the three-dimensional model of the marker comprises:
  determining a first set of voxels that corresponds with the a first one of the binary images of the marker, the first set of voxels aligned with rays projected from the first one of the binary images;
  determining a second set of voxels that corresponds with a second one of the binary images of the marker, the second set of voxels aligned with rays projected from the second one of the binary images; and
  using intersection of the first and second sets of voxels to determine the set of voxels for the three-dimensional model.

* * * * *